United States Patent [19]
Slepian et al.

[11] Patent Number: 5,947,977
[45] Date of Patent: Sep. 7, 1999

[54] APPARATUS AND POLYMERIC ENDOLUMINAL SEALING

[75] Inventors: Marvin J. Slepian, Tucson, Ariz.; Anton Schindler, Durham, N.C.

[73] Assignee: Endoluminal Therapeutics, Inc., Tucson, Ariz.

[21] Appl. No.: 08/481,646

[22] Filed: Jun. 7, 1995

Related U.S. Application Data

[62] Division of application No. 08/182,516, Jan. 14, 1994, Pat. No. 5,674,287, which is a continuation of application No. 07/651,346, which is a continuation-in-part of application No. 07/593,302, Oct. 3, 1990, and application No. 07/235,998, Aug. 24, 1988, said application No. 07/593,302, is a continuation of application No. 07/235,998, said application No. 07/651,346, filed as application No. PCT/US89/03593, Aug. 23, 1989, is a continuation-in-part of application No. 07/235,998.

[51] Int. Cl.$^6$ ...................................................... A61F 11/00
[52] U.S. Cl. .............................. 606/108; 623/1; 606/194; 604/101; 604/102; 604/113
[58] Field of Search ............................... 604/96–101, 113, 604/280, 264–266, 102–103; 606/192–194, 7–8, 13–15; 623/1

[56] References Cited

U.S. PATENT DOCUMENTS

| | | |
|---|---|---|
| 3,875,939 | 4/1975 | Bolduc et al. . |
| 4,023,559 | 5/1977 | Gaskell . |
| 4,080,969 | 3/1978 | Casey et al. . |
| 4,118,470 | 10/1978 | Casey et al. . |
| 4,595,713 | 6/1986 | St. John . |
| 4,636,195 | 1/1987 | Wolinsky ................................ 604/101 |
| 4,643,734 | 2/1987 | Lin . |
| 4,676,975 | 6/1987 | McGary et al. . |
| 4,693,704 | 9/1987 | Ogita ....................................... 604/101 |
| 4,776,337 | 10/1988 | Palmaz . |
| 4,911,163 | 3/1990 | Fina . |
| 4,969,890 | 11/1990 | Sugita et al. . |
| 5,007,926 | 4/1991 | Derbyshire . |
| 5,015,253 | 5/1991 | MacGregor . |
| 5,037,427 | 8/1991 | Harada et al. . |
| 5,059,211 | 10/1991 | Stack et al. ................................. 623/1 |
| 5,092,841 | 3/1992 | Spears ........................................ 623/1 |

(List continued on next page.)

FOREIGN PATENT DOCUMENTS

| | | |
|---|---|---|
| 0183372 | 6/1986 | European Pat. Off. . |
| 2577410 | 8/1986 | France . |
| 3640745 | 4/1987 | Germany . |
| WO 92/21354 | 12/1992 | WIPO . |

OTHER PUBLICATIONS

Dix P. Poppas et al., "Laser Welding in Urethral Surgery: Improved Results with a Protein Solder", The Journal of Urology, vol. 139, Feb., 1988, pp. 415–417.

Palmez, et al., "Normal and Stenotic Renal Arteries: Experimental Balloon–Expandable Intraluminal Stenting", Radiology: 164: 705–708 (1987).

Slepian, Marvin J., Polymeric Endoluminal Paving and Sealing: Therapeutics At The Crossroad of Biomechanics and Pharmacology, Interventional Cardiology (Textbook) Ch. 32: Ed. E.J. Topol, Saunders, Philadelphia (1990).

Boretos, John W., et al., "Segmented Polyurethane: A Polymer An Initial Evaluation For Biomedical Applications", J. Biomed Mater Res., vol. 2, pp. 121–130 (1968).

Lewis, Richard S. Sr., Hawleys Condensed Chemical Dictionary, 12th ed. Van Nostrand Reinhold Co. (1993) pp. 300, 974.

*Primary Examiner*—Mark Bockelman
*Attorney, Agent, or Firm*—Wolf, Greenfield & Sacks, P.C.

[57] ABSTRACT

A novel process for paving or sealing the interior surface of a tissue lumen by entering the interior of the tissue lumen and applying a polymer to the interior surface of the tissue lumen. This is accomplished using a catheter which delivers the polymer to the tissue lumen and causes it to conform to the interior surface of lumen. The polymer can be delivered to the lumen as a monomer or prepolymer solution, or as an at least partially preformed layer on an expansile member.

94 Claims, 8 Drawing Sheets

U.S. PATENT DOCUMENTS

| | | |
|---|---|---|
| 5,092,877 | 3/1992 | Pinchuk ................................. 623/1 |
| 5,100,429 | 3/1992 | Sunofsky et al. ..................... 623/1 |
| 5,102,417 | 4/1992 | Palmaz . |
| 5,108,416 | 4/1992 | Ryan et al. . |
| 5,139,480 | 8/1992 | Hickle et al. . |
| 5,176,638 | 1/1993 | Don Michael . |
| 5,190,540 | 3/1993 | Lee . |
| 5,192,307 | 3/1993 | Lee . |
| 5,199,951 | 4/1993 | Spears . |
| 5,232,444 | 8/1993 | Just et al. . |
| 5,242,399 | 9/1993 | Lau et al. . |
| 5,295,962 | 3/1994 | Crocker et al. . |
| 5,304,121 | 4/1994 | Sahatjian . |
| 5,344,398 | 9/1994 | Hara . |
| 5,397,307 | 3/1995 | Goodin . |
| 5,415,636 | 5/1995 | Forman . |
| 5,462,529 | 10/1995 | Simpson et al. . |
| 5,470,307 | 11/1995 | Lindall . | ns. No. 07/651,346, filed Apr. 19, 1991 (abandoned), which Ser. No. 07/651,346 is both a continuation-in-part of application Ser. No. 07/593,302, filed Oct. 3, 1990 (abandoned) which is a file-wrapper continuation of application Ser. No. 07/235, 998, filed Aug. 24, 1988 (abandoned), and which Ser. No. 07/651,346 is also a continuation-in-part of said application Ser. No. 07/235,998 (Aug. 24, 1988) via its status as a national application under 35 U.S.C. § 371 of Ser. No. 08/481,646 international application serial no. PCT/US89/ 03593, filed Aug. 23, 1989, which claims priority to said Ser. No. 07/235,998.

BACKGROUND OF THE INVENTION

This invention relates to a novel method for the in vivo paving and sealing of the interior of organs or organ components and other tissue cavities, and to apparatus and partially pre-formed polymeric products for use in this method. The tissues involved may be those organs or structures having hollow or tubular geometry, for example blood vessels such as arteries or veins, in which case the polymeric products are deposited within the naturally occurring lumen. Alternatively, the tissue may be a normally solid organ in which a cavity has been created either as a result of an intentional surgical procedure or an accidental trauma. In this case, the polymeric product is deposited in the lumen of the cavity.

Often times, the hollow or tubular geometry of organs has functional significance such as in the facilitation of fluid or gas transport (blood, urine, lymph, oxygen or respiratory gases) or cellular containment (ova, sperm). Disease processes may affect these organs or their components by encroaching upon, obstructing or otherwise reducing the cross-sectional area of the hollow or tubular elements. Additionally, other disease processes may violate the native boundaries of the hollow organ and thereby affect its barrier function and/or containment ability. The ability of the organ or structure to properly function is then severely compromised. A good example of this phenomena can be seen by reference to the coronary arteries.

Coronary arteries, or arteries of the heart, perfuse the actual cardiac muscle with arterial blood. They also provide essential nutrients and allow for removal of metabolic wastes and for gas exchange. These arteries are subject to relentless service demands for continuous blood flow throughout the life of the patient.

Despite their critical life supporting function, coronary arteries are often subject to attack through several disease processes, the most notable being atherosclerosis or hardening of the arteries. Throughout the life of the patient, multiple factors contribute to the development of microscopic and/or macroscopic vascular lesions known as plaques.

The development of a plaque lined vessel typically leads to an irregular inner vascular surface with a corresponding reduction of vessel cross-sectional area. The progressive reduction in cross-sectional area compromises flow through the vessel. For example, the effect on the coronary arteries, is a reduction in blood flow to the cardiac muscle. This reduction in blood flow, with corresponding reduction in nutrient and oxygen supply, often results in clinical angina, unstable angina or myocardial infarction (heart attack) and death. The clinical consequences of the above process and its overall importance are seen in that atherosclerotic coronary artery disease represents the leading cause of death in the United States today.

Historically, the treatment of advanced atherosclerotic coronary artery disease i.e. beyond that amenable to therapy via medication alone, involved cardio-thoracic surgery in the form of coronary artery bypass grafting (CABG). The patient is placed on cardio-pulmonary bypass and the heart muscle is temporarily stopped. Repairs are then surgically affected on the heart in the form of detour conduit grafted vessels providing blood flow around obstructions. While CABG has been perfected to be quite effective it carries with it inherent surgical risk and requires a several week, often painful recouperation period. In the United States alone approximately 150–200 thousand people are subjected to open heart surgery annually.

In 1977 a major advance in the treatment of atherosclerotic coronary artery disease occurred with the introduction of a technique known as Percutaneous Transluminal Coronary Angioplasty (PTCA). PTCA involves the retrograde introduction, from an artery in the arm or leg, up to the area of vessel occlusion, of a catheter with a small dilating balloon at its tip. The catheter is snaked through the arteries via direct fluoroscopic guidance and passed across the luminal narrowing of the vessel. Once in place, the catheter balloon is inflated to several atmospheres of pressure. This results in "cracking", "plastic" or otherwise mechanical deformation of the lesion or vessel with a subsequent increase in the cross-sectional area. This in turn reduces obstruction, and trans-tensional pressure gradients and increases blood flow.

PTCA is an extremely effective treatment with a relatively low morbidity and is rapidly becoming a primary therapy in the treatment of atherosclerotic coronary disease throughout the United States and the world. By way of example, since its introduction in 1977, the number of PTCA cases now exceeds 150,000 per annum in the United States and, for the first time in 1987, surpassed the number of bypass operations performed. Moreover, as a result of PTCA, emergency coronary artery bypass surgery is required in less than four percent of patients. Typically, atherosclerosis is a diffuse arterial disease process exhibiting simultaneous patchy involvement in several coronary arteries. Patients with this type of widespread coronary involvement, while previously not considered candidates for angioplasty, are now being treated due to technical advances and increased clinical experience.

Despite the major therapeutic advance in the treatment of coronary artery disease which PTCA represents, its success has been hampered by the development of vessel renarrowing or reclosure post dilation. During a period of hours or days post procedure, significant total vessel reclosure may develop in up to 10% of cases. This is referred to as "abrupt reclosure". However, the more common and major limitation of PTCA, is the development of progressive reversion of the vessel to its closed condition, negating any gains achieved from the procedure.

This more gradual renarrowing process is referred to as "restenosis." Post-PTCA follow-up studies report a 10–50% incidence (averaging approximately 30%) of restenosis in cases of initially successful angioplasty. Studies of the time course of restenosis have shown that it is typically an early phenomenon, occurring almost exclusively within the six months following an angioplasty procedure. Beyond this six-month period, the incidence of restenosis is quite rare. Despite recent pharmacologic and procedural advances, little success has been achieved in preventing either abrupt reclosure or restenosis post-angioplasty.

Restenosis has become even more significant with the increasing use of multi-vessel PTCA to treat complex coronary artery disease. Studies of restenosis in cases of multi-vessel PTCA reveal that after multi-lesion dilatation, the risk of developing at least one recurrent coronary lesion range from 26% to 54% and appears to be greater than that reported for single vessel PTCA. Moreover, the incidence of restenosis increases in parallel with the severity of the pre-angioplasty vessel narrowing. This is significant in light of the growing use of PTCA to treat increasingly complex multi-vessel coronary artery disease.

The 30% overall average restenosis rate has significant costs including patient morbidity and risks as well as medical economic costs in terms of follow-up medical care, repeat hospitalization and recurrent catherization and angioplasty procedures. Most significantly, prior to recent developments, recurrent restenosis following multiple repeat angioplasty attempts could only be rectified through cardiac surgery with the inherent risks noted above.

In 1987 a mechanical approach to human coronary artery restenosis was introduced by Swiss investigators referred to as, "Intracoronary Stenting". An intracoronary stent is a tubular device made of fine wire mesh, typically stainless steel. The Swiss investigators utilized a stent of the Wallsten design as disclosed and claimed in U.S. Pat. No. 4,655,771. The device can be configured in such a manner as to be of low cross-sectional area. In this "low profile" condition the mesh is placed in or on a catheter similar to those used for PTCA. The stent is then positioned at the site of the vascular region to be treated. Once in position, the wire mesh stent is released and allowed to expand to its desired cross-sectional area generally corresponding to the internal diameter of the vessel. Similar solid stents are also disclosed in U.S. Pat. No. 3,868,956 to Alfidi et al.

The metal stent functions as a permanent intravascular scaffold. By virtue of its material properties, the metal stent provides structural stability and direct mechanical support to the vascular wall. Stents of the Wallsten design are self-expanding due to their helical "spring" geometry. Recently, U.S. investigators introduced slotted steel tubes and extended spring designs. These are deployed through application of direct radial mechanical pressure conveyed by a balloon at the catheter tip. Such a device and procedure are claimed in U.S. Pat. No. 4,733,665 to Palmaz. Despite the significant limitations and potentially serious complications discussed below, this type of stenting has been successful with an almost 100% acute patency rate and a marked reduction in the restenosis rate.

The complications associated with permanent implants such as the Palmaz device result from both the choice of material, i.e., metal or stainless steel, as well as the inherent design deficiencies in the stenting devices. The major limitation lies in the permanent placement of a non-retrivable, non-degradable, foreign body in a vessel to combat restenosis which is predominantly limited to the six-month time period post-angioplasty. There are inherent, significant risks common to all permanent implant devices. Moreover, recent studies have revealed that atrophy of the media, the middle arterial layer of a vessel, may occur as a specific complication associated with metal stenting due to the continuous lateral expansile forces exerted after implantation.

These problems are even more acute in the placement of a permanent metallic foreign body in the vascular tree associated with the cardiac muscle. Coronary arteries are subjected to the most extreme service demands requiring continuous unobstructed patency with unimpeded flow throughout the life of the patient. Failure in this system will lead to myocardial infarction (heart attack) and death. In addition, the torsional and other multi-directional stresses encountered in the heart due to its continuous oscillatory/cyclic motion further amplifies the risks associated with a permanent, stiff metallic intra-arterial implant in the coronary bed.

It has been observed that, on occasion, recurrent intra-vascular narrowing has occurred post-stent placement in vessels during a period of several weeks to months. Typically, this occurs "peri-stent", i.e., immediately up or down stream from the stent. It has been suggested that this may relate to the significantly different compliances of the vessel and the stent, sometimes referred to as "compliance mismatch". Aside from changes in compliance another important mechanism leading to luminal narrowing above and below the stent may be the changes in shear forces and fluid flows encountered across the sharp transitions of the stent-vessel interface. Further supporting evidence has resulted from studies of vascular grafts which reveal a higher incidence of thrombosis and eventual luminal closure also associated with significant compliance mismatch.

To date known stent designs, i.e. tubular, wire helical or spring, scaffold design have largely been designed empirically without consideration or measurement of their radial stiffness. Recent studies measuring the relative radial compressive stiffness of known wire stents, as compared to physiologically pressurized arteries, have found them to be much stiffer than the actual biologic tissue. These studies lend support to the concept of poor mechanical biocompatibility of currently available stents.

Conventional metal stenting is severely limited since it is device dependent and necessitates a myriad of individual stents as well as multiple deployment catheters of varying lengths and sizes to accommodate individual applications. Additionally, metal stents provide a relatively rigid nonflexible structural support which is not amenable to a wide variety of endoluminal geometries, complex surfaces, luminal bends, curves or bifurcations.

These identified risks and limitations of metal stents have severely limited their utility in coronary artery applications. As of 1988, a partial self-imposed moratorium exists in the use of helical metal stents to treat human coronary artery diseases. Presently in the United States, a spring-like wire coil stent has been approved only for short term use as an emergency device for patients with irreparably closed coronary arteries following failed PTCA while in transit to emergency bypass surgery. An alternative to the use of stents has now been found which has broad applications beyond use in coronary artery applications for keeping hollow organs open and in good health.

SUMMARY OF THE INVENTION

The present invention provides a solution to the problem of restenosis following angioplasty, without introducing the problems associated with metal stents. Specifically, the invention provides a novel method for endoluminal paving and sealing (PEPS) which involves application of a polymeric material to the interior surface of the involved blood vessel. In accordance with this method, a polymeric material, either in the form of a monomer or prepolymer solution or as an at least partially pre-formed polymeric product, is introduced into the lumen of the blood vessel and positioned at the point of the original stenosis. The polymeric product is then reconfigured to conform to and maintain intimate contact with the interior surface of the blood vessel such that a paving and sealing coating is achieved.

The PEPS approach is not limited to use in connection with restenosis, however, and can also be effectively employed in any hollow organ to provide local structural support, a smooth surface, improved flow and sealing of lesions. In addition, the polymeric paving and sealing material may incorporate therapeutic agents such as drugs, drug producing cells, cell regeneration factors or even progenitor cells of the sane type as the involved organ or histologically different to accelerate healing processes. Such materials with incorporated therapeutic agents may be effectively used to coat or plug surgically or traumatically formed lumens in normally solid organs as well as the native or disease generated lumens of hollow or tubular organs.

For use in these applications, the present invention provides at least partially preformed polymeric products. These products may have any of a variety of physical shapes and sizes in accordance with the particular application. The invention also provides apparatus specially adapted for the positioning of the polymeric material, these including partially pre-formed polymeric products, at the interior surface of an organ and for the subsequent chemical or physical reconfiguration of the polymeric material such that it assumes a desired molded or customized final configuration.

DETAILED DESCRIPTION OF THE INVENTION

Figure 1:
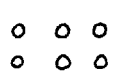
FIG. 1 shows an amorphous geometry of the PEPS polymer coating before and after deployment.
Figure 1:
Figure 1:
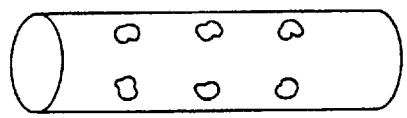

In general, PEPS involves the introduction of a polymeric material into a selected location within a lumen in tissue, i.e. an organ, an organ component or cavernous component of an organism, and the subsequent reconfiguration of the polymeric material to form a sealing in intimate and conforming contact with, or paving the interior surface. As used herein, the term "sealing" or "seal" means a coating of sufficiently low porosity that the coating serves a barrier function. The term "paving" refers to coatings which are porous or perforated. By appropriate selection of the polymeric material employed and of the configuration of the coating or paving, PEPS provides a unique customizable process, which can be utilized as a given biological or clinical situation dictates.

The basic requirements for the polymeric material to be used in the PEPS process are biocompatibility and the capacity to be chemically or physically reconfigured under conditions which can be achieved in vivo. Such reconfiguration conditions may involve heating, cooling, mechanical deformation, e.g., stretching, or chemical reactions such as polymerization or crosslinking.

Suitable polymeric materials for use in the invention include polymers and copolymers of carboxylic acids such as glycolic acid and lactic acid, polyurethanes, polyesters such as poly(ethylene terephthalate), polyamides such as nylon, polyacrylonitriles, polyphosphazines, polylactones such as polycaprolactone, and polyanhydrides such as poly[bis(p-carboxyphenoxy)propane anhydride] and other polymers or copolymers such as polyethylene, polyvinyl chloride and ethylene vinyl acetate.

Other bioabsorbable polymers could also be used either singly or in combination, or such as homopolymers and copolymers of delta-valerolactone, and p-dioxanone as well as their copolymers with caprolactone. Further, such polymers can be cross-linked with bis-caprolactone.

Preferably PEPS utilizes biodegradable polymers, with specific degradation characteristics to provide sufficient lifespan for the particular application. As noted above, a six month lifespan is probably sufficient for use in preventing restenosis; shorter or longer periods may be appropriate for other therapeutic applications.

Polycaprolactone as disclosed and claimed in U.S. Pat. No. 4,702,917 to Schindler, incorporated herein by reference, is a highly suitable bioabsorbable polymer for use in the PEPS process, particularly for prevention of restenosis. Polycaprolactone possesses adequate mechanical strength being mostly crystalline even under quenching conditions. Despite its structural stability, polycaprolactone is much less rigid than the metals used in traditional stenting. This minimizes the risk of acute vessel wall damage from sharp or rough edges. Furthermore, once poly-caprolactone has been deployed its crystalline structure will maintain a constant outside diameter. This eliminates the risks often associated with known helical or spring metal stents which after being expanded in vivo have a tendency to further expand exerting increasing pressure on the vessel wall.

The rate of bioabsorption of polycaprolactone is ideal for this application. The degradation process of this polymer has been well characterized with the primary degradation product being nonparticulate, nontoxic, 6-hydroxy hexanoic acid of low acidity. The time of biodegradation of polycaprolactone can be adjusted through the addition of various copolymers.

Polycaprolactone is a preferred polymer for use in the PEPS process because it has attained favorable clinical acceptability and is in the advanced stages of FDA approval. Polycaprolactone has a crystalline melting point of 60° C. and can be deployed in vivo via a myriad of techniques which facilitate transient heating and varying degrees of mechanical deformation or application as dictated by individual situations. This differs markedly from other bioabsorbable polymers such as polyglycolide and polylactide which melt at much higher temperatures of 180° C. and pose increased technical constraints as far as the delivery system affording polymer sculpting without deleterious tissue exposure to excessive temperatures or mechanical forces.

Polyanhydrides have been described for use as drug carrier matrices by Leong et al., J. Biomed. Mat. Res. 19, 941–955 (1985). These materials frequently have fairly low glass transition temperatures, in some cases near normal body temperature, which makes them mechanically deformable with only a minimum of localized heating. Furthermore, they offer erosion times varying from several months to several years depending on particular polymer selected.

The polymeric materials may be applied in custom designs, with varying thicknesses, lengths, and three-dimensional geometries (e.g. spot, stellate, linear, cylindrical, arcuate, spiral) to achieve varying finished geometries as depicted in FIGS. 1–8. Further, PEPS may be used to apply polymer to the inner surfaces of hollow, cavernous, or tubular biological structures (whether natural or artificially formed) in either single or multiple polymer layer configurations. PEPS may also be used, where appropriate, to occlude a tissue lumen completely.

The polymeric material used in PEPS can be combined with a variety of therapeutic agents for on-site delivery. Examples for use in coronary artery applications are anti-thrombotic agents, e.g., prostacyclin and salicylates, thrombolytic agents e.g. streptokinase, urokinase, tissue plasminogen activator (TPA) and anisoylated plasminogen-streptokinase activator complex (APSAC), vasodilating agents i.e. nitrates, calcium channel blocking drugs, anti-proliferative agents i.e. colchicine and alkylating agents, intercalating agents, growth modulating factors such as interleukins, transformation growth factor β and congeners of platelet derived growth factor, monoclonal antibodies directed against growth factors, anti-inflammatory agents, both steroidal and non-steroidal, and other agents which may modulate vessel tone, function, arteriosclerosis, and the healing response to vessel or organ injury post intervention. In applications where multiple polymer layers are used different pharmacological agents could be used in different polymer layers. Moreover, PEPS may be used to effect pharmaceutical delivery focally within the vessel wall, i.e. media.

The polymeric material in accordance with the invention may also have incorporated in it living cells to serve any of several purposes. For examples, the cells may be selected, or indeed designed using principles of recombinant DNA technology, to produce specific agents such as growth factors. In such a way, a continuously regenerating supply of a therapeutic agent may be provided without concerns for stability, initial overdosing and the like.

Figure 9:
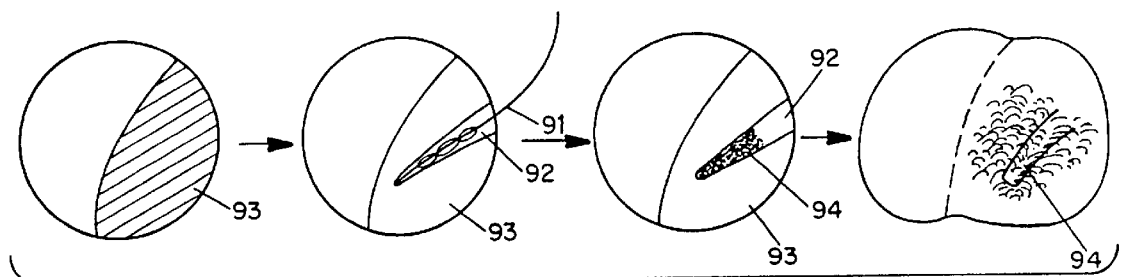
FIG. 9 shows a process for using PEPS to treat an artificially created tissue lumen.

Cells incorporated in the polymeric material may also be progenitor cells corresponding to the type of tissue in the lumen treated or other cells providing therapeutic advantage. For example, liver cells might be implanted in the polymeric material within a lumen created in the liver of a patient to facilitate regeneration and closure of that lumen. This might be an appropriate therapy in the case where scar tissue or other diseased, e.g. cirrhosis, fibrosis, cystic disease or malignancy, or non-functional tissue segment has formed in the liver or other organ and must be removed. The process of carrying out such treatment, shown schematically in FIG. 9, involves first inserting a catheter 91 into a lumen 92 within a diseased organ segment 93. The lumen 92 can be a native vessel, or it can be a man-made lumen, for example a cavity produced by a laser. The catheter 91 is used to introduce a polymeric plug 94 into the lumen 92. The catheter is then removed, leaving the plug 94 in place to act as a focus for new growth stemming from cells implanted along with the polymeric plug 94. If the desire is for a more tubular structure, the plug 94 can be appropriately reconfigured.

Optional additions to the polymeric material such as barium, iodine or tantalum salts for X-ray radio-opacity allow visualization and monitoring of the coating.

The technique of PEPS preferably involves the percutaneous application of a polymeric material, preferably a biodegradable polymer such as polycaprolactone, either alone or mixed with other biodegradable polymeric materials, which may optionally contain various pharmaceutical agents for controlled sustained release of the pharmaceutical or for selective soluble factor adsorption and trapping. The polymeric material is typically applied to the inside of an organ surface employing combined thermal and mechanical means to manipulate the polymeric material. Although capable of being used during surgery, PEPS will generally be applied without the need for a surgical procedure using some type of catheter, for example novel modifications of the known catheter technology described above for (PTCA). PEPS is preferably applied using a single catheter with multiple balloons and lumens. The catheter should be of relatively low cross-sectional area. Typically a long thin tubular catheter manipulated using fluoroscopic guidance can access deep into the interior of organ or vascular areas.

The polymer may be deployed in the interior of the vessel or organ from the surface or tip of the catheter. Alternatively, the polymer could be positioned on a balloon such as that of a standard angioplasty balloon catheter. Additionally, the polymer could be applied by spraying, extruding or otherwise internally delivering the polymer via a long flexible tubular device consisting of as many lumens as a particular application may dictate.

Figure 10A:
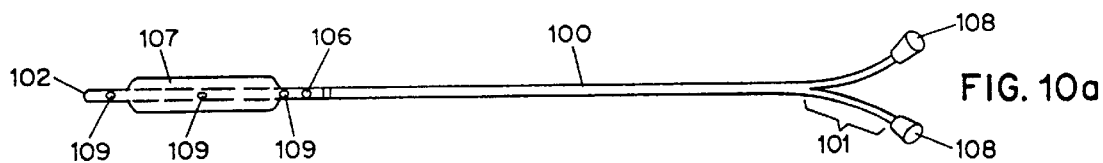
FIGS. 10a–10e show two lumen catheters according to the invention.

The simplest PEPS coating is a continuous coating over a designated portion of a tissue lumen. Such a coating can be applied with a simple two lumen catheter such as those shown in FIGS. 10a–10c. Looking first to FIG. 10a, a suitable catheter is formed from a tubular body 100 having a proximal end 101 and a distal end 102. The interior of the tubular body 100 is divided into two conduits 103 and 104 which extend from the proximal end 101 to apertures 105 and 106 in the tubular body. (FIGS. 10b and 10c) Conduits 103 and 104 thus connect apertures 105 and 106 with the proximal end 101 of the tubular body 100 to allow fluid flow therebetween. The proximal ends of conduits 103 and 104 are preferably equipped with connectors 108 which allow connection with fluid supplies. Pressure connectors such as Luer® locks are suitable.

The catheter may also include markers 109 in one or more locations to aid in locating the catheter. These markers can be, for example, fluoroscopic radio-opaque bands affixed to the tubular body 100 by heat sealing.

Figure 10B:
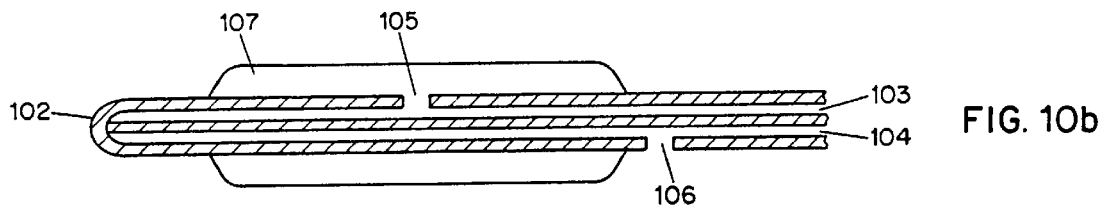
Figure 10C:
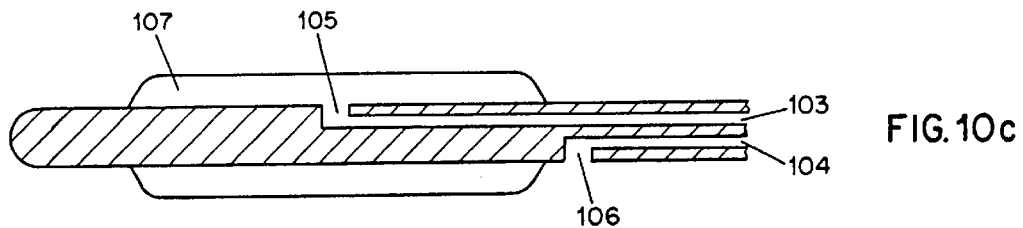

The catheter shown in FIGS. 10b and 10c has an expansile member in the form of an inflatable balloon 107 disposed over the distal aperture 105. In use, an at least a partially preformed polymeric layer or partial layer is positioned over the balloon 107 and the catheter is inserted into an appropriate position in the tissue lumen. Fluid flow through conduit 103 will cause the balloon 107 to inflate, stretch and deform the polymer layer until it comes into contact with the walls of the tissue lumen. The other aperture 106 and conduit 104 are used to control the reconfiguration of the polymeric sleeve, for example by supplying a flow of heated liquid to soften the sleeve and render it more readily stretchable or to stimulate polymerization of a partially polymerized sleeve.

Figure 10D:
Figure 10E:
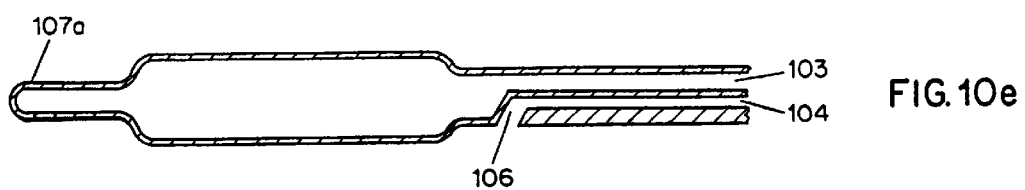

Variations on this basic two lumen catheter can be made, examples of which are shown in FIGS. 10d and 10e. For example FIG. 10d has a shapable wire affixed to the tip of the catheter to aid in insertion and a traumatic and directed passage through the organism, i.e. to act as a guide wire. In FIG. 10e, the expansile member is incorporated as part of the tubular body as a continuous element, preferably a unitary element. In this case, the distal tip 107a of the catheter expands in response to fluid flow in conduit 103. Conduit 104 can be formed by bonding in or on the extruded catheter body a piece of the same or different material in a tubular form. This type of design can also be used in more complicated multi-lumen catheters discussed below.

The polymeric material may take the form of a sleeve designed to be readily insertable along with the catheter into the tissue lumen, and then to be deployed onto the wall of the lumen to form the coating. This deployment can be accomplished by inflating a balloon, such as balloon 107 using fluid flow through conduit 103. Inflation of balloon 107 stretches the polymeric sleeve causing it to press against the walls of the tissue lumen and acquire a shape corresponding to the lumen wall. This shape is then fixed, and the cather removed leaving behind a polymeric paving or seal on the lumen wall.

The process of fixing the shape of the polymeric material can be accomplished in several ways, depending on the character of the original polymeric material. For example, a partially polymerized material can be expanded using the balloon after which the conditions are adjusted such that polymerization can be completed, e.g., by increasing the local temperature or providing UV radiation through an optical fiber. A temperature increase might also be used to soften a fully polymerized sleeve to allow expansion and facile reconfiguration and local molding, after which it would "freeze" in the expanded position when the heat source is removed. Of course, if the polymeric sleeve is a plastic material which will permanently deform upon stretching (e.g., polyethylene, polyethylene terephthalate, nylon or polyvinyl chloride), no special fixation procedure is required.

As depicted in FIG. 10b, local heating can be provided by a flow of heated liquid directly into the tissue lumen. Thermal control can also be provided, however, using a fluid flow through or into the expansile member or using a "leaky" partially perforated balloon such that temperature control fluid passes through the expansile member, or using electrical resistive heating using a wire running along the length of the catheter body in contact with resistive heating elements. This type of heating element can make use of DC or radio frequency (RF) current or external RF or microwave radiation. Other methods of achieving temperature control can also be used, including laser heating using an internal optical fiber (naked or lensed) or thermonuclear elements.

Figure 11A:
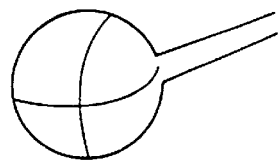
FIGS. 11a–11d show surface contours of expansile members useful in catheters according to the invention.
Figure 11C:
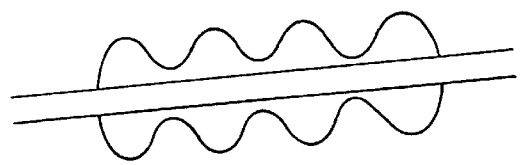
Figure 11B:
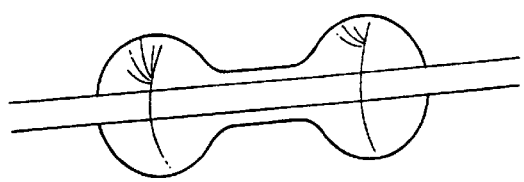
Figure 11D:
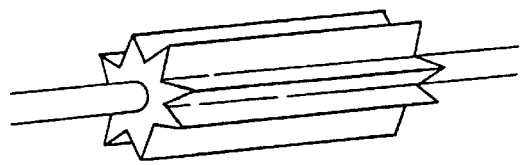
Figure 12A:
FIGS. 12a–12g show three catheters according to the invention.
Figure 12B:
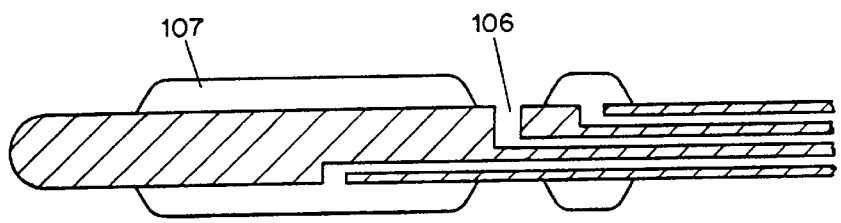
Figure 12C:
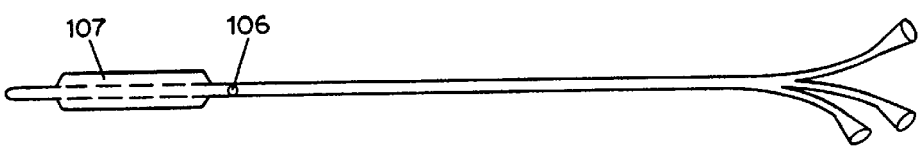
Figure 12D:
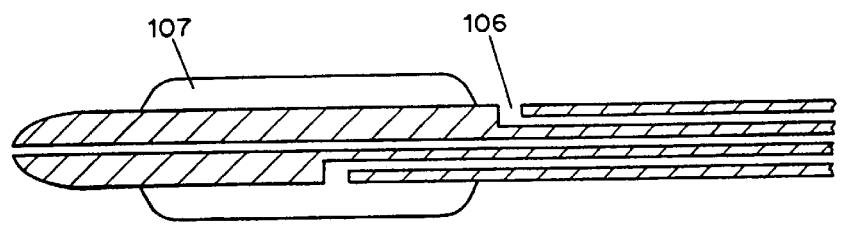
Figure 12E:
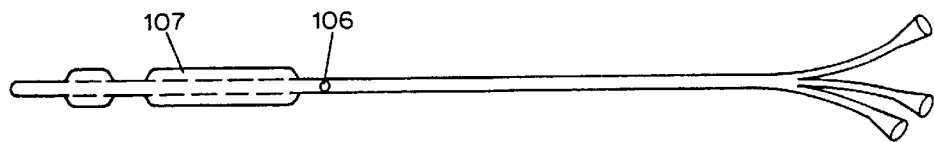
Figure 12F:
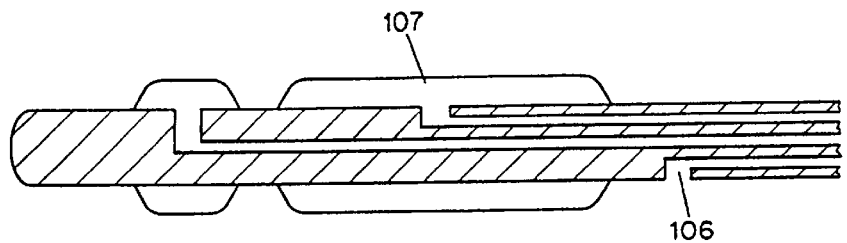
Figure 12G:
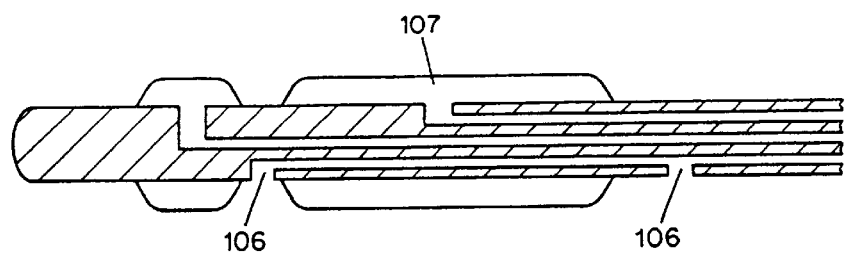
Figure 13A:
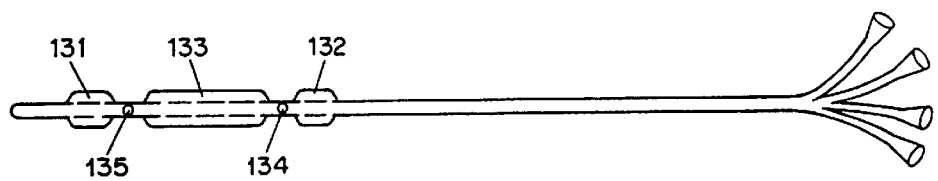
FIGS. 13a–13h show four lumen catheters according to the invention.
Figure 13B:
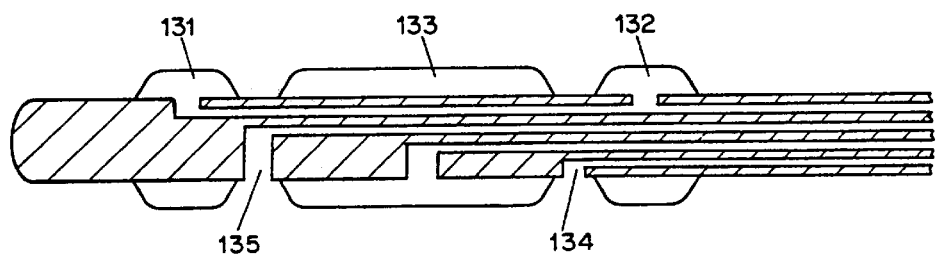
Figure 13C:
Figure 13D:
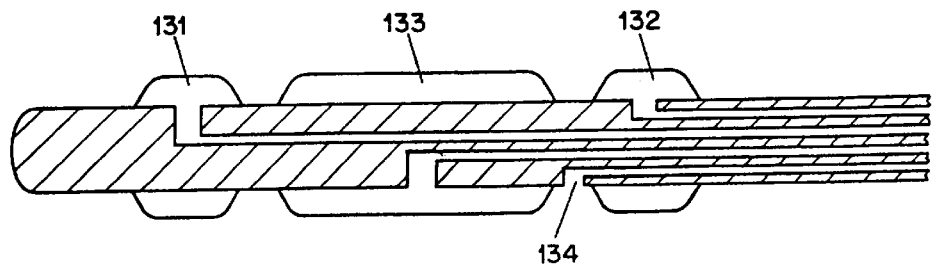
Figure 13E:
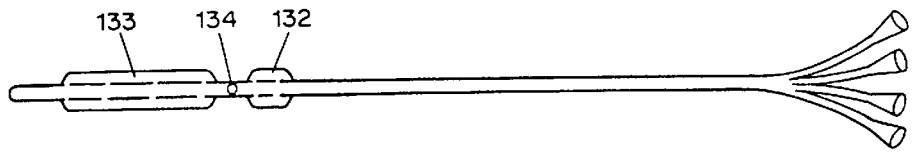
Figure 13F:
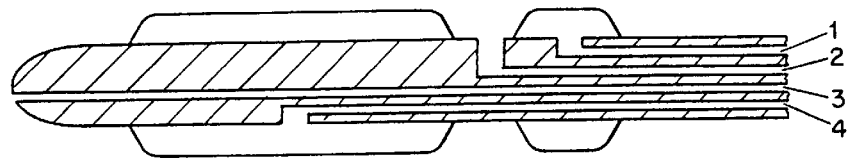
Figure 13G:
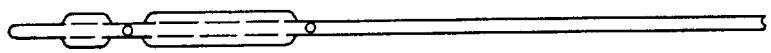
Figure 13H:
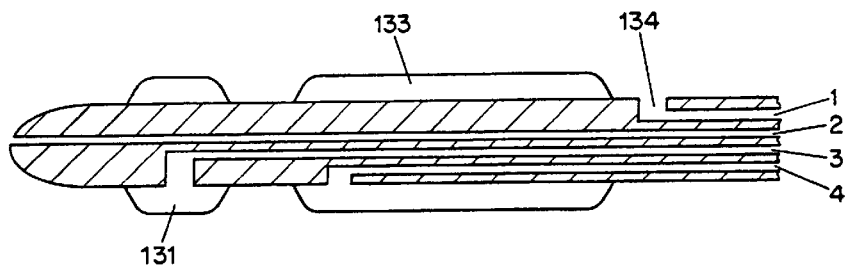

In addition to the smooth shape shown in FIG. 10, the balloon used to configure the polymer can have other surface shapes for formation of the coatings to provide specific polymeric deployment patterns. For example, the balloon may be a globular shape intended for deployment from the tip of a catheter device. (FIG. 11a) Such an arrangement would be preferred when the paving operation is being carried out in a cavity as opposed to a tubular organ. The balloon might also be thickened at the ends (FIG. 11b) or substantially helical (FIG. 11c) providing a variation in coating thickness along the length of the paved or sealed area. Such a configuration might prove advantageous in the case where additional structural support is desired and to provide a tapered edge to minimize flow disruption. Variations in coating thickness which provide ribs running the length of the tissue lumen might be achieved using a stellate balloon (FIG. 11d). This type of polymer coating would be useful in the case where additional structural support is desirous combined with more continuous flow properties. In addition balloon shape may facilitate insertion in some cases.

Variations in the ultimate configuration of the PEPS coating can also be achieved by using more complex deployments of the polymer on the expansile member. For example, the polymer can be in the form of a perforated tubular sleeve, a helical sleeve or in the form of discontinuous members of various shapes. These may be affixed to the expansile member directly, for example with an adhesive or by suction through perforations and the like, or to an overcoating such as dissolvable gauze-like or paper sheath (i.e. spun saccharide) or held in place by a retractable porous sheath which will be removed with the catheter after application.

Figure 20A:
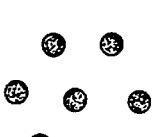
FIGS. 20a–20e show enmeshed discontinuous polymeric material arrayed on a catheter with a retractable sheath.
Figure 20B:
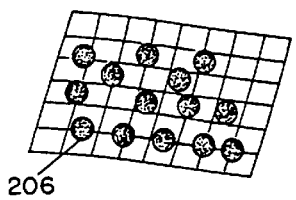
Figure 20C:
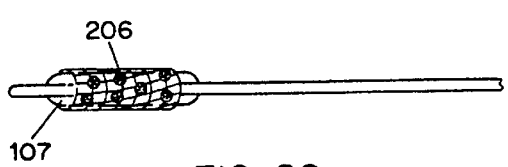
Figure 20D:
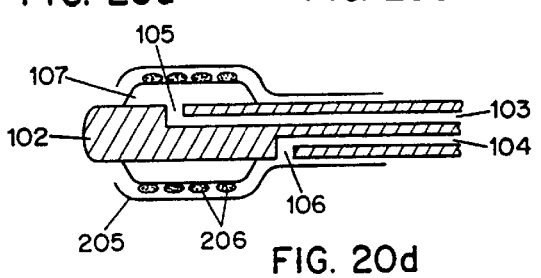
Figure 20E:
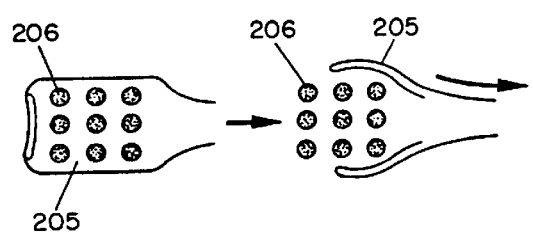

For example, FIG. 20(a) shows an array of polymer dots. These dots are enmeshed in a dissolvable mesh substrate FIG. 20(b) which in turn is wrapped around the expansile member 107 of a catheter according to the invention (FIG. 20c). An exemplary two lumen catheter is shown in FIG. 20d (numbered as in FIG. 10b) where a retractable sheath 205 surrounds the polymer dots 206 for insertion. When the catheter reaches the application site, the sheath 205 is retracted (FIG. 20e) and the balloon 107 expanded.

Figure 14A:
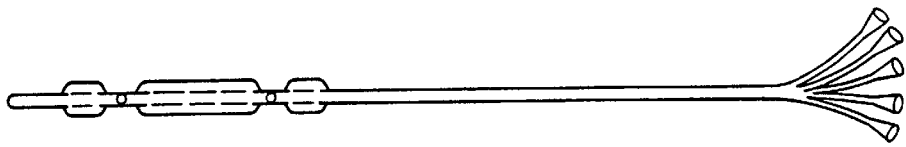
FIGS. 14a and 14b show five lumen catheters according to the invention.
Figure 14B:
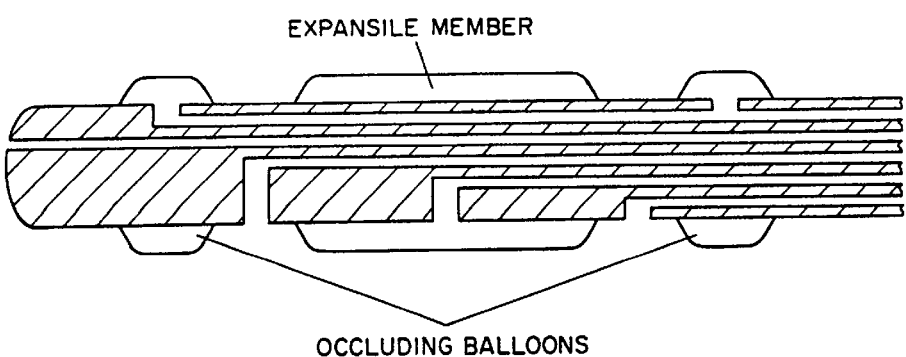

It will be recognized, that the catheter depicted in FIG. 20d represents a minimalist approach to PEPS catheter design, and that additional lumens may be included within the catheter body to provide conduits for inflation of positioning balloons, optical fibers, additional polymer molding balloons, temperature control means, and passage of steering or guide wires or other diagnostic devices, e.g. ultrasound catheter, or therapeutic devices such as atherectomy catheter or other lesion modifying device. For example, three lumen catheters (FIGS. 12a–12d), four lumen catheters (FIGS. 13a–13h), five lumen catheters (FIGS. 14a and 14b), six lumen catheters (FIGS. 15a and 15b) and seven lumen catheters (FIGS. 16a and 16b) might be employed. A retractable sheath may also be provided which extends over the polymer during insertion to prevent premature separation of the polymer from the catheter. In addition, catheters may have telescoping sections such that the distance between the occluding balloons can be varied.

Figure 15A:
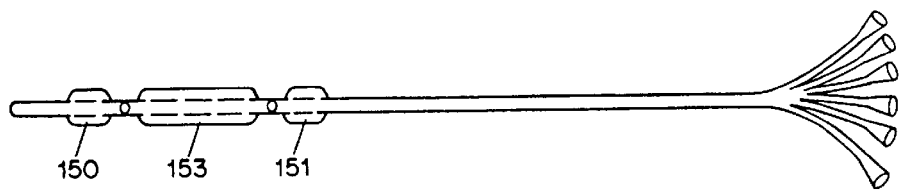
FIGS. 15a–15b show six lumen catheters according to the invention.
Figure 15B:
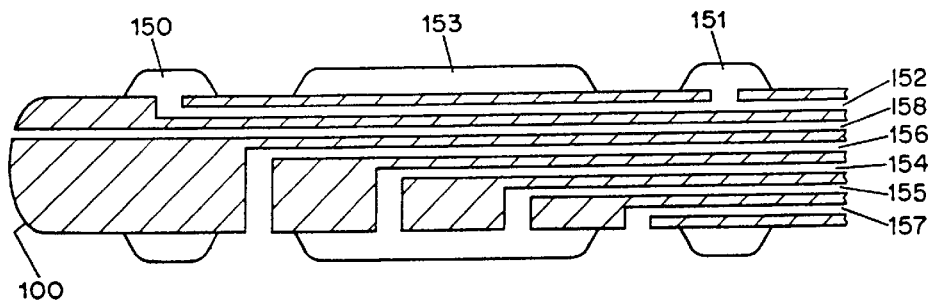
Figure 16A:
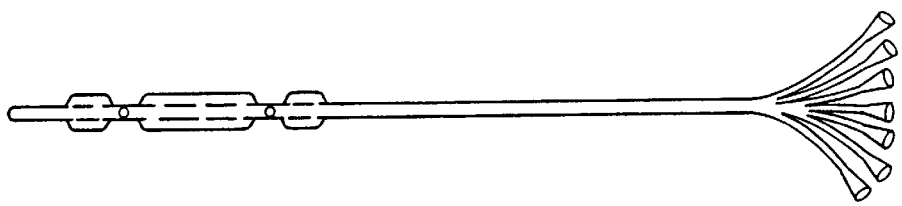
FIGS. 16a and 16b show seven lumen catheters according to the invention.
Figure 16B:
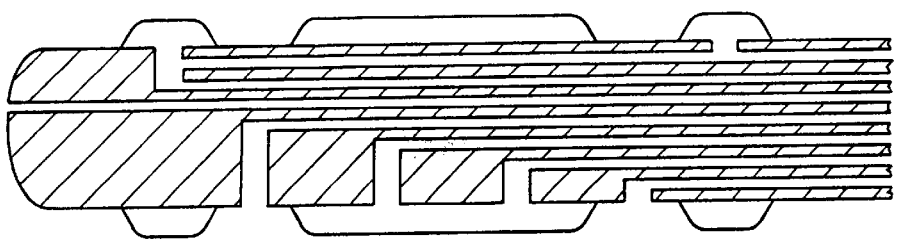

Looking for example at the six lumen catheters in FIGS. 15a and 15b, two positioning balloons 150 and 151, both connected to conduit 152. Positioning balloons 150 and 151 serve to fix the position of the tubular body 100 within a tissue lumen and isolate the portion of the tissue lumen between them where the PEPS coating will be applied. Expansile member 153 is provided with circulating flow via conduits 154 and 155. This can be used to provide temperature control to the isolated portion of the tissue lumen, as well as acting to configure the polymeric coating formed by expanding a polymeric sleeve and other deployed form fitted over expansile member 153. In the catheter shown in FIG. 15b, a temperature control solution or a therapeutic solution is advantageous provided through conduit 156, with conduit 157 acting as a drain line (or vice versa) to allow flow of fluid through the isolated portion of the tissue lumen ("superfusion"). Such a drain line is not required, however, and a simple infusion cather could omit one of the conduits 156 or 157 as in the five lumen designs of FIGS. 14a and 14b. The sixth conduit 158 is also optional, but can be advantageously used for guide wires, diagnostic or therapeutic device passage, or distal fluid perfusion. If conduit 158 has an aperture proximal to balloon 151, it can be used as a by-pass conduit for passive perfusion during occlusion.

The incorporation in the catheter of positioning balloons which occlude a section of the tissue lumen makes it possible to utilize solutions of monomers or prepolymers and form the coating in situ. Looking for example at four lumen catheters shown in FIG. 13b, an isolation zone is created by inflating balloons 131 and 132 so that they press against the tissue lumen. While expansile member 133 could be used to deform a polymeric sleeve or other deployment form, it can also be used to define the size and environmental conditions (e.g. temperature) of the lumen region.

Application of the polymeric material may be accomplished by extruding a solution of monomers or prepolymers through the aperture 134 to coat or fill the tissue lumen. The formation of a polymer coating can be controlled by introducing crosslinking agents or polymerization catalysts together with the monomer or prepolymer solution and then altering the conditions such that polymerization occurs. Thus, a flow of heated fluid into expansile member 133 can increase the local temperature to a level sufficient to induce or accelerate polymerization. Alternatively, the monomer/prepolymer solution might be introduced cold, with metabolic temperature being sufficient to induce polymerization. The other aperture 135 acts as a drain line in superfusion applications.

Figure 21A:
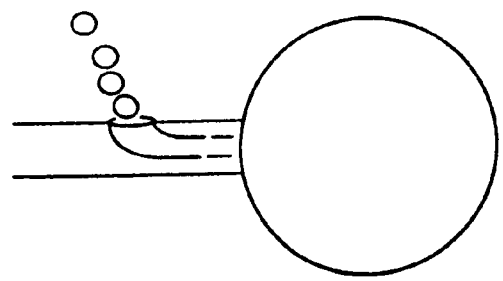
FIGS. 21a–21c show variations in apertures for polymer delivery to a tissue lumen.
Figure 21B:
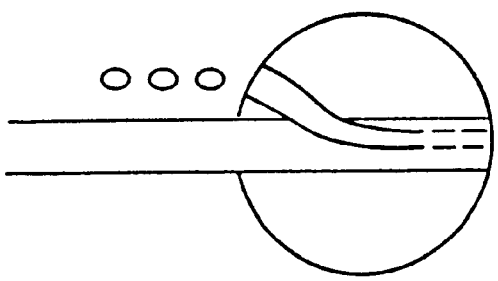
Figure 21C:
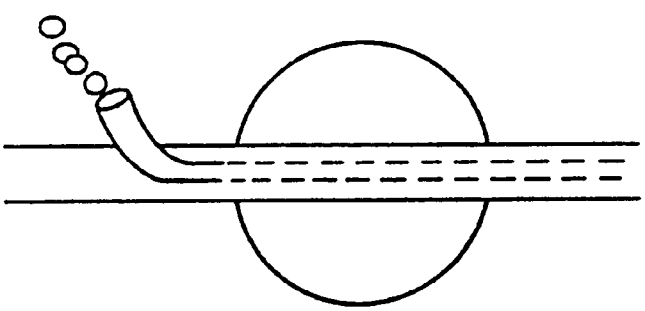

The polymeric material can be introduced to the tissue lumen through a simple aperture in the side of the tube as shown in FIG. 21a, or through a raised aperture (FIG. 21b). A shaped nozzle which is extendable away from the surface of the tubular body (FIG. 21c) can also be used. The material can be extruded through, or it can be subjected to flow restriction to yield a spray application. This flow restriction can be adjustable to control the spray. In addition, localized acceleration at the tip of the nozzle can be used, for example, via a piezoelectric element to provide sprayed application.

The catheters bodies for use in this invention can be made of any known material, including metals, e.g. steel, and thermoplastic polymers. Occluding balloons may be made from compliant materials such as latex or silicone, or non-compliant materials such as polyethyleneterephthalate (PET). The expansile member is preferably made from non-compliant materials such as PET, PVC, polyethylene or nylon. The expansile member may optionally be coated with materials such as silicones, polytetra-fluoroethylene (PTFE), hydrophilic materials like hydrated hydrogels and other lubricious materials to aid in separation of the polymer coating.

In addition to arteries, i.e. coronary, femeroiliac, carotid and vertebro-basilar, the PEPS process may be utilized for other applications such as paving the interior of veins, ureters, urethrae, bronchi, biliary and pancreatic duct systems, the gut, eye and spermatic and fallopian tubes. The sealing and paving of the PEPS process can also be used in other direct clinical applications even at the coronary level. These include but are not limited to the treatment of abrupt vessel reclosure post PCTA, the "patching" of significant vessel dissection, the sealing of vessel wall "flaps", i.e. secondary to catheter injury or spontaneously occurring, the sealing of aneurysmal coronary dilations associated with various arteritidies. Further, PEPS provides intra-operative uses such as sealing of vessel anostomoses during coronary artery bypass grafting and the provision of a bandaged smooth polymer surface post endarterectomy.

The unique pharmaceutical delivery function of the PEPS process may be readily combined with "customizable" deployment geometry capabilities to accommodate the interior of a myriad of complex organ or vessel surfaces. Most importantly, this customized geometry can be made from structurally stable yet biodegradable polymers. The ability to tailor the external shape of the deployed polymer through melted polymer flow into uneven surface interstices, while maintaining a smooth interior surface with good flow characteristics, will facilitate better structural support for a variety of applications including eccentric coronary lesions which by virtue of their geometry are not well bridged with conventional metal stents.

As noted above, the polymer substrate used in PEPS may be fashioned, for example, out of extruded tubes of polycaprolactone and/or copolymers. The initial predeployment design and size of the polymer sleeve will be dictated by the specific application based upon the final deployed physical, physiological and pharmacological properties desired.

For coronary artery application, predeployment tubes of about 10 to 20 mm in length and about 1 to 2 mm in diameter would be useful. The initial wall thickness of the resulting in vivo polymer layer may be varied depending upon the nature of the particular application. In general coating procedures require polymer layers of about 0.005 mm to 0.50 mm while layers which are designed to give structural support can vary from 0.05 mm to 5.0 mm.

The polymer tube walls may be processed prior to insertion with either laser or chemical etching, pitting, slitting or perforation depending upon the application. In addition, the shape of any micro (10 nm to 1 $\mu$m) or macro (>1 $\mu$m up to about 15 $\mu$m) perforation may be further geometrically modified to provide various surface areas on the inner versus outer seal surface. The surfaces of the predeployed polymer may be further modified with bound, coated, or otherwise applied agents, i.e., cyanoacrylates or biological adhesives such as those derived from fungal spores, the sea mussel or autologous fibrinogen adhesive derived from blood.

For PEPS applications involving the coronary arteries, the polymer tubes (if in an initial tubular configuration), should preferably have perforations or pores, of a size dictated by the particular application. This will ensure a symmetric expansion of the encasing polymeric sealant. By using a fragmented tubular polymer surface with corresponding expansions along predicted perforations (i.e., the slots) a significant mechanical stabililty is provided. In addition, this minimizes the amount of foreign material placed within the vessel.

Depending upon the polymer and pharmaceutical combination and the configuration, PEPS may be used to coat or bandage the organ inner surface with a thin adhesive partitioning polymer film or layer of about 0.005 mm to 0.50 mm. Biodegradable polymers thus applied to an internal organ or vessel surface will act as an adherent film "bandage." This improved surface, with desirable rheologic and adherence properties, facilitates improved fluid or gas transport in and through the body or lumen of the vessel or hollow organ structure and acts to reinstate violated native surfaces and boundaries.

The ultimate in vivo deployed geometry of the polymer dictates the final function of the polymer coating. The thinner applications allow the polymer film to function as a coating, sealant and/or partitioning barrier, bandage, and drug depot. Complex internal applications of thicker layers of polymer, such as intra-vessel or intra-luminal applications, may actually provide increased structural support and depending on the amount of polymer used in the layer may actually serve in a mechanical role to maintain vessel or organ potency.

For example, lesions which are comprised mostly of fibromuscular components have a high degree of viscoelastic recoil. These lesions would require using the PEP process to apply an intraluminal coating of greater thickness and extent so as to impart more structural stability thereby resisting vessel radial compressive forces. The PEPS process in this way provides structural stability and is generally applicable for the maintenance of the intraluminary geometry of all tubular biological organs or substructure. It may be used in this way following the therapeutic return of normal architecture associated with either balloon dilation (PTCA), atherectomy, lesion spark, thermal or other mechanical erosion, "G-lazing", welding or laser recanalization.

An important feature of the PEPS technique is the ability to customize the application of the polymer to the internal surface of a vessel or organ as dictated by the particular application. This results in a variety of possible geometries of polymer as well as a variety of forms. These multi-geometry, multi-form polymer structures may be adjusted to correspond to particular functions. (FIGS. 1–8)

Figure 2:
FIG. 2 shows a stellate geometry of the PEPS polymer coating before and after deployment.
Figure 2:
Figure 2:
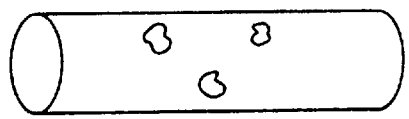
Figure 3:
FIG. 3 shows a linear feathered polymer strip applied to "one" wall before and after deployment.
Figure 3:
Figure 3:
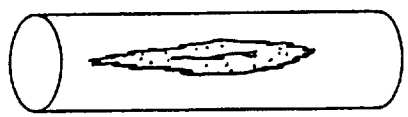
Figure 4:
FIG. 4 shows a large patch of sprayed on polymer material before and after deployment.
Figure 4:
Figure 4:
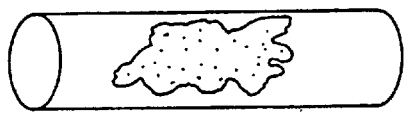
Figure 5:
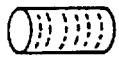
FIG. 5 shows a porous tubular form geometry before and after deployment.
Figure 5:
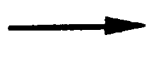
Figure 5:
Figure 6:
FIG. 6 shows a spot geometry of the PEPS process before and after deployment.
Figure 6:
Figure 6:
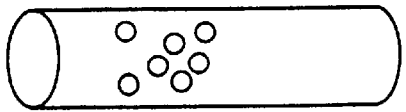
Figure 7:
FIG. 7 shows a spiral form application of the PEPS process before and after deployment.
Figure 7:
Figure 7:
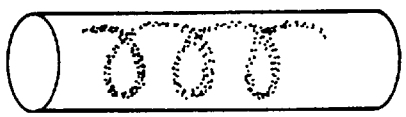
Figure 8:
FIG. 8 shows an arcuate (radial, arc) patch geometry of the PEPS polymer before and after deployment.
Figure 8:
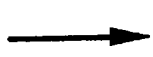
Figure 8:
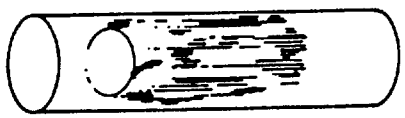

With particular reference to FIGS. 1–8 the PEPS process may be affectuated so that the focal application of polymer to the vessel or organ results in either an amorphous geometry, FIG. 1, stellate geometry, FIG. 2, or spot geometry, FIG. 6. Additional geometries could include a linear feathered polymer strip applied to a particular area of the vessel wall as shown in FIG. 3. FIG. 4 shows a large patch of polymer which can be sprayed on using a variety of known techniques. Another form of the PEPS application to be utilized in instances, e.g., where structural stability need be imparted to the vessel would be the porous tubular form shown in FIG. 5. Other types of PEPS applications which would impart structural stability to the vessel would be the spiral form application shown in FIG. 7, or the arcuate (radial, arc) patch as shown in FIG. 8.

Conversely, in cases where the severely denuded lesions have irregular surfaces with less fibromuscular components, the PEPS process can be used to provide only a thin polymer film to act as a bandage.

The PEPS' process is significantly different and is conceptually an advance beyond stents and stenting in achieving vessel patency. Stents have been designed with the underlying primary function of providing a relatively stiff structural support to resist post PTCA, vessel reclosure caused by the vessel's spring-like characteristics. It has been increasingly demonstrated that cellular and biochemical mechanisms as opposed to physical "spring-like" coils, are of a much greater significance in preventing vessel reclosure and PEPS addresses these mechanisms.

The specific object and features of the PEPS process are best understood by way of illustration with reference to the following examples and figures.

EXAMPLE 1

Figure 17:
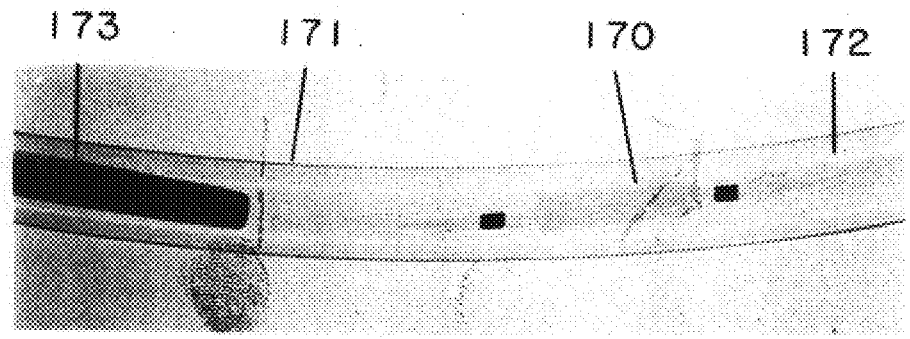
FIG. 17 shows a distal occlusion catheter and a polymer delivery catheter in a vessel.

The invention may be readily understood through a description of an experiment performed in vitro using a mock blood vessel made from transparent plastic tubing using a heat-balloon type deployment catheter reference to FIG. 17.

The balloon delivery catheter 170 is first positioned in the vessel 171 at the area of the occlusion. Before insertion, a polycaprolactone polymer sleeve 172 containing additives, e.g. to aid X-ray radio-opacity, for drug delivery or to promote surface adhesion, is placed in a low profile condition surrounding a balloon at the distal end of the delivery catheter 170. The delivery catheter with the polycaprolactone tube is then inserted balloon end first into the vessel 171 and manipulated into position, i.e., the area of the vessel to be treated.

A separate occlusion catheter 173 is employed to restrict "blood" flow through the vessel. The distal end of the occlusion catheter 173 is inflated to create a stagnant column of "blood" in the vessel around the balloon delivery catheter and polycaprolactone tube. Saline solution at about 60–80° C. is injected through a lumen in the occlusion catheter 173 or the delivery catheter 170 in the case of using a catheter according to the invention into the area surrounding the delivery catheter, balloon and polycaprolactone tube. Once the polycaprolactone tube becomes pliable, the delivery catheter balloon is inflated to push the polycaprolactone sleeve out against the interior wall thereby locally sealing and/or paving the vessel.

The polycaprolactone expands and/or flows, conforming to the inner surface of the vessel, flowing into and filling in surface irregularities thereby creating a "tailored" fit. Further, the deployed interior surface of the PEPS polymer is smooth providing an increased vessel (lumen) cross-section diameter and a rheologically advantageous surface with improved blood flow. Upon removal of heated saline solution the polymer recrystallizes to provide a paved surface of the vessel wall interior.

The deployment catheter balloon is then deflated leaving the polycaprolactone layer in place. The balloon section of the occlusion catheter is deflated and, blood flow was allowed to return to normal and the deployment catheter was removed leaving the recrystallized polycaprolactone layer in place within the vessel.

Over the course of time the polycaprolactone seal will become covered with a proteinaceous biologic thin film coat. Depending upon the exact seal chemical composition, the polymer will then biodegrade, at a predetermined rate and "dissolve" into the bloodstream or be absorbed into the vessel wall. While in intimate contact with the vessel wall, pharmacological agents if embedded or absorbed in the polycaprolactone will have a "downstream" effect if released slowly into the bloodstream or may have a local effect on the blood vessel wall, thereby facilitating healing of the angioplasty site, controlling or reducing exuberant medial smooth muscle cell proliferation, promoting effective lesion endothelialyation and reducing lesion thrombogenicity.

EXAMPLE 2

Figure 18:
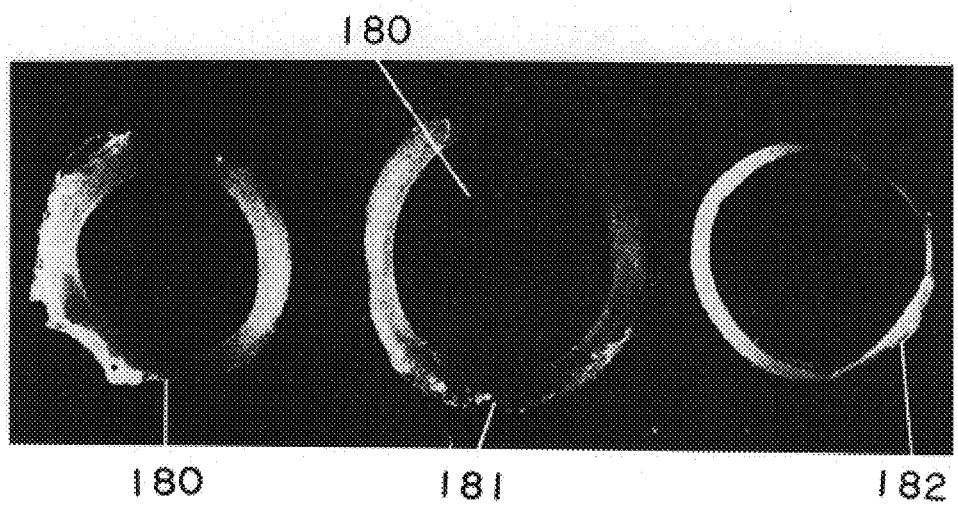
FIG. 18 shows in cross-section a polymeric sleeve before insertion in a blood vessel; the sleeve after insertion in the vessel and after expansion.
Figure 19:
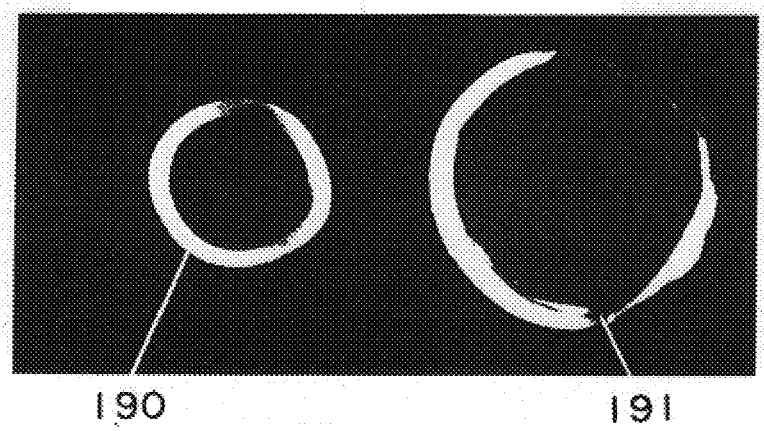
FIG. 19 is a cross-sectional comparison of an initial polymeric sleeve and an expanded polymeric sleeve.

Polycaprolactone in an initial macroporous tubular configuration was placed in a low profile form in bovine coronary arteries and canine carotid arteries. In the process of deployment the vessels were purposely overextended and sealed through thermal and mechanical deformation of the polymer. FIG. 18 shows a cross-section of the polymer tube 180 before insertion in the bovine artery, after insertion in the artery 181, and after expansion 182. The initial polymer tube 180, is smaller in diameter than the artery 181. After deployment, the thin film of polymer 182 can be seen coating the inner surface of the sealed vessel with the vessel remaining erect. The vessel remained dilated to about 1.5 times the original diameter because of the ability of the polymer to keep it fixed. FIG. 19 shows a cross-section of the polymer before insertion 190 and removed after insertion and reconfiguration 191 in a canine artery. This figure clearly shows the stretching and thinning of the polymer wall.

All polymer sealed vessels remained dilated with a thin layer of macroporous polymer providing a new barrier surface between the vessel lumen and the vessel wall constituents. The unsealed portion of the vessels did not remain dilated.

These examples demonstrate that the PEPS process may if desired provide polymer application with a relatively large degree of surface area coverage and an effective polymer barrier shield. As such, the polymer barrier-shield may, if desired, impart sufficient structural stability to maintain a selected vessel diameter. The selected final vessel diameter at which a vessel is sealed is dictated by the particular physiological variables and therapeutic goals which confront the PEPS user.

The geometry of the pre and post PEPS application sites may be readily varied. PEPS may be used to merely coat an existing vessel or organ geometry. Alternatively, the PEPS process may be used to impart structural stability to a vessel or organ the geometry of which was altered prior to the PEPS application. In addition, the PEPS process may itself alter the geometry of the vessel or organ by shaping the geometry. With reference to FIG. 18 this latter process was used to expand the vessel 181.

A specific and important attribute of the PEPS technique and the polymers which ate employed is the significantly lower degree of compliance mismatch or similarities of stiffness (inverse of compliance) between the vessel and the polymer seal as compared to metal stents. The vessel damage from compliance mismatch discussed above may be eliminated by the PEPS process utilizing a variety of available polymers. Additionally, compliance mismatch greatly modifies the characteristics of fluid wave transmission along the vessel with resultant change in local flow properties, development of regional change in shear forces and a subsequent vessel wall hypertrophy which acts to reduce vessel cross-sectional area and reduces blood flow. Further, the substructural elimination of compliance mismatch of the PEPS technique at first minimizes and then, upon dissolution eliminates local flow abnormalities and up and downstream transition zone hypertrophy associated with metal stenting.

PEPS has the flexibility of being safely and effectively used prophylactically at the time of initial PTCA in selected patients or being incorporated as part of the original dilation procedure as a second stage prophylactic vessel surface "finishing" process. For example, the invasive cardiologist may apply the PEPS technique on a wide clinical basis after the first episodes of restenosis. In addition, because the PEPS technique significantly aids in the vascular healing process post intervention, it may be readily used prophylactically after initial angioplasty prior to any incidence of restenosis. This would free the patient from the risks of repeat intracoronary procedure as well as those associated with metal stenting.

We claim:

1. Catheter apparatus comprising:
   an elongate tubular shaft having a distal end insertable into a patient and a proximal end adapted to remain outside of the patient;
   an article-forming element at the distal end of the shaft;
   a polymeric article positioned on the article-forming element that is formable into a layer of biodegradable polymeric material in intimate and conforming contact with an irregularly contoured tissue surface that is near the distal end of the shaft when the shaft is inserted into a patient; and
   a source of temperature control in thermal communication with the polymeric article.

2. Catheter apparatus as recited in claim 1, wherein the article-forming element is radially expandable.

3. Catheter apparatus as recited in claim 2, further comprising a lumen associated with the shaft that provides fluid communication between the distal end and the proximal end, wherein the article-forming element is connected via the lumen to a source of pressurized fluid.

4. Catheter apparatus as recited in claim 2, wherein the article-forming element is a dilatation balloon.

5. Catheter apparatus as recited in claim 1, further comprising a lumen associated with the shaft that provides fluid communication between the distal end and the proximal end, wherein the source of temperature control comprises a source of a temperature-controlled fluid and the lumen is a fluid conduit between the source of temperature-controlled fluid and the polymeric article.

6. Catheter apparatus as recited in claim 5, wherein the temperature-controlled fluid comprises a fluid at a temperature greater than that of normal patient temperature.

7. Catheter apparatus as recited in claim 5, further comprising a drain lumen associated with the shaft that is a fluid conduit between the polymeric article and the proximal end of the shaft.

8. Catheter apparatus as recited in claim 1, further comprising a first and a second lumen associated with the shaft that provide fluid communication between the distal end and the proximal end, wherein the article-forming element comprises a radially-expandable balloon disposed about the shaft in alignment with an aperture of the first lumen, the source of temperature control comprises a source of temperature-controlled fluid, and the second lumen is a fluid conduit between the source of temperature-controlled fluid and the balloon.

9. Catheter apparatus as recited in claim 8, further comprising a drain lumen associated with the shaft that has an aperture in alignment with the balloon, and that is a fluid conduit between the balloon and the proximal end of the shaft.

10. Catheter apparatus as recited in claim 1, wherein the source of temperature control comprises a heat source.

11. Catheter apparatus as recited in claim 1, wherein the polymeric article is made of a material selected from the group consisting of polymers and copolymers of carboxylic acids, polyurethanes, polyesters, polyamides, polyacrylonitriles, polyphosphazines, polylactones, polyanhydrides, polyethylenes, polyvinyl chlorides, ethylene vinyl acetate, delta-valerolactone, and p-dioxanone.

12. Catheter apparatus as recited in claim 1, wherein the polymeric article contains a therapeutic agent.

13. Catheter apparatus as recited in claim 1, wherein the polymeric article contains a living cell.

14. Catheter apparatus as recited in claim 1, wherein the polymeric article is defined by at least two polymer layers.

15. Catheter apparatus as recited in claim 14, wherein the at least two layers are each comprised of a different composition.

16. Catheter apparatus as recited in claim 1, wherein the polymeric article is further coated at least in part.

17. Catheter apparatus as recited in claim 16, wherein the coating is biocompatible.

18. Catheter apparatus as recited in claim 1, further comprising at least one radiopaque marker.

19. Catheter apparatus comprising:
   an elongate tubular shaft having a distal end insertable into a patient and a proximal end adapted to remain outside of the patient;
   an article-forming element at the distal end of the shaft; and
   a polymeric article positioned on the article-forming element that is formable into a layer of biodegradable polymeric material in intimate and conforming contact with an irregularly contoured tissue surface that is near the distal end of the shaft when the shaft is inserted into a patient,
   wherein the polymeric article is non-fluent at normal patient temperature, becomes fluent when its temperature is altered from normal patient temperature to an application temperature, and becomes non-fluent when its temperature returns from the application temperature to normal patient temperature.

20. Catheter apparatus as in claim 19, wherein the article-forming element is a dilatation balloon.

21. Catheter apparatus as in claim 19, further comprising a source of temperature control in thermal communication with the polymeric article.

22. Catheter apparatus as claimed in claim 21, wherein the temperature-controlled fluid comprises a fluid at a temperature greater than that of normal patient temperature.

23. Catheter apparatus as recited in claim 19, wherein the article is made of a material selected from the group consisting of polymers and copolymers of carboxylic acids, polyurethanes, polyesters, polyamides, polyacrylonitriles, polyphosphazines, polylactones, polyanhydrides, polyethylenes, polyvinyl chlorides, ethylene vinyl acetate, delta-valerolactone, and p-dioxanone.

24. Catheter apparatus as recited in claim 19, wherein the polymeric article contains a therapeutic agent.

25. Catheter apparatus as recited in claim 19, wherein the polymeric article contains a living cell.

26. Catheter device as in claim 19, wherein the polymeric article is further coated, at least in part, with a biocompatible coating.

27. Catheter apparatus comprising:
   an elongate tubular shaft having a distal end insertable into a patient and a proximal end adapted to remain outside of the patient;
   an article-forming element at the distal end of the shaft;
   a polymeric article positioned on the article-forming element that is formable into a layer of biodegradable polymeric material in intimate and conforming contact with an irregularly contoured tissue surface that is near the distal end of the shaft when the shaft is inserted into a patient; and
   a lumen associated with the shaft that provides fluid communication between the distal end and the proximal end, wherein the article-forming element comprises a radially-expandable balloon disposed on the shaft in alignment with the lumen and is in fluid communication via the lumen with a source of pressurized fluid, the polymeric article is non-fluent at normal patient temperature, becomes fluent at an application temperature that is greater than normal patient temperature, and becomes non-fluent when its temperature returns from the application temperature to normal patient temperature, and the apparatus further comprises a source of heated fluid in fluid communication with the polymeric article.

28. Catheter apparatus comprising:
   an elongate tubular shaft having a distal end insertable into a patient and a proximal end adapted to remain outside of the patient;
   an emitter of electromagnetic radiation near the distal end of the shaft;
   an article-forming element at the distal end of the shaft; and
   a polymeric article positioned on the article-forming element that is formable into a layer of biodegradable polymeric material in intimate and conforming contact with an irregularly contoured tissue surface that is near the distal end of the shaft when the shaft is inserted into a patient,
   wherein the emitter of electromagnetic radiation is positioned in optical communication with the polymeric article and wherein the article is made of a material selected from the group consisting of polymers of carboxylic acids, polyurethanes, polyesters, polyamides, polyacrylonitriles, polyphosphazines, polylactones, polyanhydrides, polyethylenes, polyvinyl chlorides, ethylene vinyl acetate, delta-valerolactone, and p-dioxanone.

29. Catheter apparatus as recited in claim 28, wherein the article is made of a material selected from the group consisting of polymers and copolymers of carboxylic acids, polyurethanes, polyesters, polyamides, polyacrylonitriles, polyphosphazines, polylactones, polyanhydrides, polyethylenes, polyvinyl chlorides, ethylene vinyl acetate, delta-valerolactone, and p-dioxanone.

30. Catheter apparatus as recited in claim 28, wherein the polymeric article contains a therapeutic agent.

31. Catheter apparatus as recited in claim 28, wherein the polymeric article contains a living cell.

32. Catheter apparatus as in claim 28, wherein the polymeric article is further coated, at least in part, with a biocompatible coating.

33. Catheter apparatus comprising:
   an elongate tubular shaft having a distal end insertable into a patient and a proximal end adapted to remain outside of the patient;
   an emitter of electromagnetic radiation near the distal end of the shaft;
   an article-forming element at the distal end of the shaft; and
   a polymeric article that contains a therapeutic agent positioned on the article-forming element, formable into a layer of biodegradable polymeric material in intimate and conforming contact with an irregularly contoured tissue surface that is near the distal end of the shaft when the shaft is inserted into a patient, wherein the emitter of electromagnetic radiation is positioned in optical communication with the polymeric article.

34. Catheter apparatus comprising:

an elongate tubular shaft having a distal end insertable into a patient and a proximal end adapted to remain outside of the patient;

an emitter of electromagnetic radiation near the distal end of the shaft;

an article-forming element at the distal end of the shaft; and a polymeric article that contains living cells, formable into a layer of biodegradable polymeric material in intimate and conforming contact with an irregularly contoured tissue surface that is near the distal end of the shaft when the shaft is inserted into a patient, positioned on the article-forming element, wherein the emitter of electromagnetic radiation is positioned in optical communication with the polymeric article.

35. Catheter apparatus comprising:

an elongate tubular shaft having a distal end insertable into a patient and a proximal end adapted to remain outside of the patient;

an emitter of electromagnetic radiation near the distal end of the shaft;

an article-forming element at the distal end of the shaft; and a polymeric article, formable into a layer of biodegradable polymeric material in intimate and conforming contact with an irregularly contoured tissue surface that is near the distal end of the shaft when the shaft is inserted into a patient, positioned on the article-forming element, wherein the emitter of electromagnetic radiation is positioned in optical communication with the polymeric article and the polymeric article is non-fluent at normal patent temperature, becomes fluent when its temperature is raised above normal patient temperature, and becomes non-fluent when its temperature returns to normal patient temperature.

36. Catheter apparatus comprising:

an elongate tubular shaft having a distal end insertable into a patient and a proximal end adapted to remain outside of the patient;

an emitter of electromagnetic radiation near the distal end of the shaft;

a radially expandable article-forming element at the distal end of the shaft;

a polymeric article, formable into a layer of biodegradable polymeric material in intimate and conforming contact with an irregularly contoured tissue surface that is near the distal end of the shaft when the shaft is inserted into a patient, positioned on the article-forming element wherein the emitter of electromagnetic radiation is positioned in optical communication with the polymeric article; and a lumen associated with the shaft that provides fluid communication between the distal end and the proximal end, wherein the radially expandable article-forming element is connected via the lumen to a source of pressurized fluid.

37. Catheter apparatus comprising:

an elongate tubular shaft having a distal end insertable into a patient and a proximal end adapted to remain outside of the patient;

a radially expandable balloon at the distal end of the shaft;

a polymeric article, formable into a layer of biodegradable polymeric material in intimate and conforming contact with an irregularly contoured tissue surface that is near the distal end of the shaft when the shaft is inserted into a patient, positioned on the balloon; and an emitter of electromagnetic radiation near the distal end of the shaft positioned in optical communication with the polymeric article.

38. Catheter apparatus as recited in claim 37, further comprising a drain lumen associated with the shaft that is a fluid conduit between the polymeric article and the proximal end of the shaft.

39. Catheter apparatus as recited in claim 37, further comprising a second lumen, wherein the article-forming element comprises a radially-expandable balloon disposed about the shaft in alignment with an aperture of the second lumen, the apparatus further comprising a drain lumen associated with the shaft that has an aperture in alignment with the balloon, and that is a fluid conduit between the balloon and the proximal end of the shaft.

40. Catheter apparatus comprising:

an elongate tubular shaft having a distal end insertable into a patient and a proximal end adapted to remain outside of the patient;

a lumen associated with the shaft that provides fluid communication between the distal end and the proximal end;

a reservoir of pre-polymer fluid in fluid communication with the distal end of the shaft via the lumen that is formable into a layer of biodegradable polymeric material in intimate and conforming contact with an irregularly contoured tissue surface that is near the distal end of the shaft when the shaft is inserted into a patient; and a heat source in thermal communication with the distal end of the shaft.

41. Catheter apparatus as recited in claim 40, wherein the heat source comprises a source of heated fluid, the apparatus further comprising a heated fluid lumen associated with the shaft that is a fluid conduit between the source of heated fluid and the distal end of the shaft.

42. Catheter apparatus as recited in claim 41, further comprising a drain lumen associated with the shaft that is a fluid conduit between the distal end of the shaft and the proximal end of the shaft.

43. Catheter apparatus comprising:

an elongate tubular shaft having a distal end insertable into a patient and a proximal end adapted to remain outside of the patient;

a lumen associated with the shaft that provides fluid communication between the distal end and the proximal end;

a reservoir of pre-polymer fluid in fluid communication with the distal end of the shaft via the lumen that is formable into a layer of biodegradable polymeric material in intimate and conforming contact with an irregularly contoured tissue surface that is near the distal end of the shaft when the shaft is inserted into a patient; and an emitter of electromagnetic radiation near the distal end of the shaft.

44. Catheter apparatus as recited in claim 43, further comprising a laser and an optical fiber connecting the emitter to the laser.

45. Catheter apparatus as recited in claim 43, further comprising a radially-expandable occlusion element near the distal end of the shaft.

46. Catheter apparatus as recited in claim 45, wherein the occlusion element comprises a radially-expandable balloon.

47. Catheter apparatus as recited in claim 45, wherein the lumen includes an aperture at the distal end of the shaft located distally relative to the occlusion element.

48. Catheter apparatus comprising:
   an elongate tubular shaft having a distal end insertable into a patient and a proximal end adapted to remain outside of the patient;
   a lumen associated with the shaft that provides fluid communication between the distal end and the proximal end;
   a reservoir of pre-polymer fluid in fluid communication with the distal end of the shaft via the lumen, formable into a layer of biodegradable polymeric material in intimate and conforming contact with an irregularly contoured tissue surface that is near the distal end of the shaft when the shaft is inserted into a patient;
   a radially-expandable occlusion element near the distal end of the shaft; and
   a molding element near the distal end of the shaft.

49. Catheter apparatus as recited in claim 48, wherein the molding element comprises a radially-expandable balloon.

50. Catheter apparatus as recited in claim 48, wherein the molding element is positioned distally relative to the occlusion element.

51. Catheter apparatus as recited in claim 48, wherein the molding element is movable axially relative to the occlusion element.

52. Catheter apparatus as recited in claim 48, further comprising a source of temperature control in thermal communication with the distal end of the shaft.

53. Catheter apparatus as recited in claim 52, wherein the source of temperature control comprises a source of a temperature-controlled fluid, the apparatus further comprising a temperature-controlled fluid lumen associated with the shaft that is a fluid conduit between the source of temperature-controlled fluid and the distal end of the shaft.

54. Catheter apparatus as recited in claim 53, wherein the temperature-controlled fluid comprises a fluid at a temperature greater than that of normal patient temperature.

55. Catheter apparatus as recited in claim 53, wherein the molding element comprises a radially-expandable balloon disposed about the shaft in alignment with the temperature-controlled fluid lumen aperture, and the apparatus further comprises a drain lumen associated with the shaft that has an aperture in alignment with the balloon and that is a fluid conduit between the balloon and the proximal end of the shaft.

56. Catheter apparatus as recited in claim 52, wherein the source of temperature control comprises a heat source.

57. Catheter apparatus as recited in claim 48, further comprising near the distal end of the shaft an emitter of electromagnetic radiation.

58. Catheter apparatus as recited in claim 57, wherein the emitter is optically connected to a laser via an optical fiber.

59. Catheter apparatus comprising:
   an elongate tubular shaft having a distal end insertable into a patient and a proximal end adapted to remain outside of the patient;
   a lumen associated with the shaft that provides fluid communication between the distal end and the proximal end;
   a reservoir of pre-polymer fluid in fluid communication with the distal end of the shaft via the lumen, formable into a layer of biodegradable polymeric material in intimate and conforming contact with an irregularly contoured tissue surface that is near the distal end of the shaft when the shaft is inserted into a patient;
   a radially-expandable proximal occlusion element near the distal end of the shaft and a radially-expandable distal occlusion element on the shaft positioned distally relative to the proximal occlusion element.

60. Catheter apparatus as recited in claim 59, wherein the lumen has an aperture on the shaft between the proximal occlusion element and the distal occlusion element.

61. Catheter apparatus as recited in claim 59, wherein the proximal and distal occlusion elements are movable axially relative to each other.

62. Catheter apparatus as recited in claim 59, wherein the distal occlusion element comprises a radially-expandable balloon.

63. Catheter apparatus as recited in claim 59, further comprising a molding element between the proximal occlusion element and the distal occlusion element.

64. Catheter apparatus as recited in claim 63, wherein the distance between the proximal and distal occlusion elements can be varied.

65. Catheter apparatus as recited in claim 63, wherein the molding element comprises a radially-expandable balloon.

66. Catheter apparatus as recited in claim 65, wherein the source of temperature control comprises a source of a temperature-controlled fluid, the apparatus further comprising a temperature-controlled fluid lumen associated with the shaft that is a fluid conduit between the source of temperature-controlled fluid and the distal end of the shaft.

67. Catheter apparatus as recited in claim 66, wherein the temperature-controlled fluid comprises a fluid at a temperature greater than that of normal patient temperature.

68. Catheter apparatus as recited in claim 66, wherein the molding element comprises a radially-expandable molding balloon disposed about the shaft in alignment with the temperature-controlled fluid lumen aperture, and the apparatus further comprises a drain lumen associated with the shaft that has an aperture in alignment with the balloon and that is a fluid conduit between the balloon and the proximal end of the shaft.

69. Catheter apparatus as recited in claim 63, further comprising a source of temperature control in thermal communication with the distal end of the shaft.

70. Catheter apparatus as recited in claim 69, wherein the source of temperature control comprises a heat source.

71. Catheter apparatus as recited in claim 63, further comprising near the distal end of the shaft an emitter of electromagnetic radiation.

72. Catheter apparatus as recited in claim 71, further comprising a laser and an optical fiber connecting the laser to the emitter.

73. A catheter device for application of a biodegradable polymeric coating to a tissue lumen comprising a tubular body having proximal and distal ends, which tubular body defines a lumen divided into a plurality of sublumens, each sublumen extending from the proximal end of the tubular body toward the distal end of the tubular body and connecting to at least one aperture in the tubular body whereby each sublumen forms a conduit for fluid flow between at least one aperture in the tubular body and the proximal end of the tubular body, wherein at least one of said sublumens is connected to a reservoir containing a monomer or pre-polymer-containing liquid, whereby the biodegradable polymeric coating is formed by delivering the monomer or pre-polymer-containing liquid through the sublumen to the tissue lumen, and wherein the device includes two occluding balloons, one disposed toward the proximal end of the tubular body from the aperture of the sublumen which is connected to the reservoir, and the other disposed toward the distal end of the tubular body from the aperture of the sublumen which controls delivery of polymeric coating material, whereby the occluding balloons together act to at least partially occlude a portion of the tissue lumen.

74. A catheter device for application of a biodegradable polymeric coating to a tissue lumen comprising biodegradable polymer coating material and a tubular body having proximal and distal ends, which tubular body defines a plurality of lumens each lumen extending from the proximal end of the tubular body toward the distal end of the tubular body and connecting to at least one aperture in the tubular body whereby each lumen forms a conduit for fluid flow between at least one aperture in the tubular body and the proximal end of the tubular body, the catheter constructed and arranged such that fluid flow through at least one of said lumens can control delivery of the biodegradable polymeric coating material to the tissue lumen, wherein the device includes two occluding balloons, one disposed toward the proximal end of the tubular body from the aperture of the lumen which controls delivery of polymeric coating material, and the aperture toward the distal end of the tubular body from the aperture of the lumen which controls delivery of polymeric coating material, whereby the occluding balloons together act to at least partially occlude a portion of the tissue lumen.

75. A catheter device as in claim 74, wherein the distal aperture of the lumen controlling polymer delivery is constructed and arranged to provide flow acceleration.

76. A catheter device as in claim 74, wherein the lumen which controls polymer delivery forms a conduit between a vessel containing a monomer or pre-polymer solution for the polymer coating and the tissue lumen.

77. A catheter device as in claim 76, further comprising an expansible member disposed around the tubular body in alignment with an expansible member inflation aperture and between the positioning balloons, whereby the thickness and surface configuration of the polymer coating is controlled by inflation of the expansible member.

78. A catheter device as in claim 74, wherein an expansible member is disposed around the tubular body in alignment with the aperture of the lumen that controls polymer delivery, whereby fluid flow through the lumen that controls polymer delivery inflates the expansible member.

79. A catheter device as in claim 78, wherein the expansible member has a contoured surface whereby a molded shape is imparted to the polymeric coating.

80. A catheter device as in claim 74, wherein the polymeric material includes one or more therapeutic agents.

81. A catheter device as in claim 74, wherein inflation of the two occluding balloons is independently controllable.

82. A catheter device for application of a biodegradable polymeric coating to a tissue lumen comprising biodegradable polymer coating material and a tubular body having proximal and distal ends, which tubular body defines a plurality of lumens each lumen extending from the proximal end of the tubular body toward the distal end of the tubular body and connecting to at least one aperture in the tubular body whereby each lumen forms a conduit for fluid flow between at least one aperture in the tubular body and the proximal end of the tubular body, the catheter constructed and arranged such that fluid flow through at least one of said lumens can control delivery of the biodegradable polymeric coating material to the tissue lumen, wherein an expansible member is disposed around the tubular body in alignment with the aperture of the lumen that controls polymer delivery, whereby fluid flow through the lumen that controls polymer delivery inflates the expansible member, and wherein a partial or complete layer of polymeric coating material is disposed around the expansible member, whereby expansion of the balloon causes the polymeric material to coat the tissue lumen.

83. A catheter device as in claim 82, wherein a continuous, perforated or helical polymeric sleeve is disposed around the expansible member, whereby expansion of the balloon causes the polymeric material to expand to coat the tissue lumen.

84. A catheter device as in claim 82, wherein the polymeric coating material is discontinuous and disposed on a mesh support.

85. A catheter device for application of a biodegradable polymeric coating to a tissue lumen comprising biodegradable polymer coating material and a tubular body having proximal and distal ends, which tubular body defines a plurality of lumens each lumen extending from the proximal end of the tubular body toward the distal end of the tubular body and connecting to at least one aperture in the tubular body whereby each lumen forms a conduit for fluid flow between at least one aperture in the tubular body and the proximal end of the tubular body, the catheter constructed and arranged such that fluid flow through at least one of said lumens can control delivery of the biodegradable polymeric coating material to the tissue lumen, wherein the device includes a heating element, whereby the polymeric coating material can be heated prior or subsequent to delivery to the tissue lumen.

86. A catheter device for application of a biodegradable polymeric coating to a tissue lumen comprising biodegradable polymer coating material and a tubular body having proximal and distal ends, which tubular body defines a plurality of lumens each lumen extending from the proximal end of the tubular body toward the distal end of the tubular body and connecting to at least one aperture in the tubular body whereby each lumen forms a conduit for fluid flow between at least one aperture in the tubular body and the proximal end of the tubular body, the catheter constructed and arranged such that fluid flow through at least one of said lumens can control delivery of the biodegradable polymeric coating material to the tissue lumen, wherein the device includes an optical fiber whereby light can be delivered to the polymeric coating material.

87. A catheter device for application of a biodegradable polymeric coating to a tissue lumen comprising biodegradable polymer coating material and a tubular body having proximal and distal ends, which tubular body defines a plurality of lumens each lumen extending from the proximal end of the tubular body toward the distal end of the tubular body and connecting to at least one aperture in the tubular body whereby each lumen forms a conduit for fluid flow between at least one aperture in the tubular body and the proximal end of the tubular body, the catheter constructed and arranged such that fluid flow through at least one of said lumens can control delivery of the biodegradable polymeric coating material to the tissue lumen, wherein the device includes a mechanically retractable protective sheath.

88. A catheter device for application of a biodegradable polymeric coating material to a tissue lumen comprising biodegradable polymeric coating material and a tubular body having proximal and distal ends, which tubular body defines a plurality of lumens, each lumen extending from the proximal end of the tubular body toward the distal end of the tubular body and connected to at least one aperture in the tubular body, each lumen forming a conduit for fluid flow between at least one aperture in the tubular body and the proximal end of the tubular body, wherein at least one lumen is constructed and arranged to allow the biodegradable polymeric coating material to be reconfigured in the tissue lumen by a fluid flowed through said at least one lumen, wherein the device includes two occluding balloons, one disposed toward the proximal end of the tubular body from the aperture of the lumen which controls delivery of polymeric coating material, and the other disposed toward the distal end of the tubular body from the aperture of the lumen which controls delivery of polymeric coating material, whereby the occluding balloons together act to at least partially occlude a portion of the tissue lumen.

89. A catheter device as in claim 88, wherein an expansible member is disposed around the tubular body in alignment with the aperture of the lumen that controls polymer delivery, whereby fluid flow through the lumen that controls polymer delivery inflates the expansible member.

90. A catheter device as in claim 88, wherein the distal aperture of the lumen controlling polymer delivery is shaped to provide flow acceleration.

91. A catheter device for application of a biodegradable polymeric coating material to a tissue lumen comprising biodegradable polymeric coating material and a tubular body having proximal and distal ends, which tubular body defines a plurality of lumens, each lumen extending from the proximal end of the tubular body toward the distal end of the tubular body and connected to at least one aperture in the tubular body, each lumen forming a conduit for fluid flow between at least one aperture in the tubular body and the proximal end of the tubular body, wherein at least one lumen is constructed and arranged to allow the biodegradable polymeric coating material to be reconfigured in the tissue lumen by a fluid flowed through said at least one lumen, wherein the device includes a heating element, whereby the polymeric coating material can be heated prior or subsequent to delivery to the tissue lumen.

92. A catheter device for application of a biodegradable polymeric coating material to a tissue lumen comprising biodegradable polymeric coating material and a tubular body having proximal and distal ends, which tubular body defines a plurality of lumens, each lumen extending from the proximal end of the tubular body toward the distal end of the tubular body and connected to at least one aperture in the tubular body, each lumen forming a conduit for fluid flow between at least one aperture in the tubular body and the proximal end of the tubular body, wherein at least one lumen is constructed and arranged to allow the biodegradable polymeric coating material to be reconfigured in the tissue lumen by a fluid flowed through said at least one lumen, wherein the device includes an optical fiber whereby light can be delivered to the polymeric coating material.

93. A catheter device as in claim 92, wherein the polymeric material includes one or more therapeutic agents.

94. A catheter device for application of a biodegradable polymeric coating to a tissue lumen comprising biodegradable polymer coating material and a tubular body having proximal and distal ends, which tubular body defines a plurality of lumens each lumen extending from the proximal end of the tubular body toward the distal end of the tubular body and connecting to at least one aperture in the tubular body whereby each lumen forms a conduit for fluid flow between at least one aperture in the tubular body and the proximal end of the tubular body, the catheter constructed and arranged such that fluid flow through at least one of said lumens can control delivery of the biodegradable polymeric coating material to the tissue lumen, wherein the distal aperture of the lumen is constructed and arranged to provide flow acceleration and shaped to provide sprayed application.

* * * * *

UNITED STATES PATENT AND TRADEMARK OFFICE
CERTIFICATE OF CORRECTION

PATENT NO. :   5,947,977
DATED      :   September 7, 1999
INVENTOR(S) :  Marvin J. Slepian et al.

It is certified that error appears in the above-identified patent and that said Letters Patent is hereby corrected as shown below:

On the cover page, In the title, please change the title to --Apparatus for Polymeric Endoluminal Sealing--.

In column 23, line 27, please change "aperture" to --other disposed--.

Signed and Sealed this

Fourth Day of July, 2000

Attest:

Q. TODD DICKINSON

*Attesting Officer*   *Director of Patents and Trademarks*